(12) United States Patent
Burk et al.

(10) Patent No.: US 6,960,769 B2
(45) Date of Patent: Nov. 1, 2005

(54) INFRARED MEASURING APPARATUS AND METHOD FOR ON-LINE APPLICATION IN MANUFACTURING PROCESSES

(75) Inventors: Gary Neil Burk, Powell, OH (US); Thomas Michael Domin, Galena, OH (US); Rodney Dale Maxson, Columbus, OH (US); Dennis Charles Daugherty, Grove City, OH (US); Steven Perry Sturm, Dublin, OH (US)

(73) Assignee: ABB Inc., Columbus, Inc., OH (US)

( * ) Notice: Subject to any disclaimer, the term of this patent is extended or adjusted under 35 U.S.C. 154(b) by 216 days.

(21) Appl. No.: 10/264,080

(22) Filed: Oct. 3, 2002

(65) Prior Publication Data

US 2004/0065829 A1 Apr. 8, 2004

(51) Int. Cl.[7] .................................................. G01J 5/02
(52) U.S. Cl. ............................ 250/339.07; 250/339.06; 250/338.1; 250/336.1; 250/339.1; 250/339.12; 250/353; 250/228; 356/429
(58) Field of Search ....................... 250/339.07, 339.06, 250/338.1, 339.1, 336.1, 339.12, 353, 228; 356/429

(56) References Cited

U.S. PATENT DOCUMENTS

| | | | |
|---|---|---|---|
| 3,455,637 A | 7/1969 | Howard | |
| 3,793,524 A | 2/1974 | Howarth | |
| 4,027,161 A * | 5/1977 | Williams et al. | 250/339.06 |
| 4,052,615 A * | 10/1977 | Cho | 250/341.8 |
| 4,710,807 A | 12/1987 | Chikama | |
| 4,733,078 A | 3/1988 | Sturm | |
| 4,823,008 A * | 4/1989 | Sturm | 250/339.04 |
| 5,067,810 A | 11/1991 | Bu-Abbud | |
| 5,124,552 A * | 6/1992 | Anderson | 250/339.04 |
| 5,243,402 A * | 9/1993 | Weber et al. | 356/429 |
| 5,870,926 A | 2/1999 | Saito et al. | |
| 5,967,048 A * | 10/1999 | Fromson et al. | 101/463.1 |
| 6,215,575 B1 | 4/2001 | Tuchman | |
| 6,365,899 B1 | 4/2002 | Arai et al. | |
| 6,696,685 B2 * | 2/2004 | Schumacher | 250/341.1 |
| 6,717,148 B2 * | 4/2004 | Kansakoski et al. | 250/339.11 |
| 2001/0033490 A1 * | 10/2001 | Koyama et al. | 362/293 |

FOREIGN PATENT DOCUMENTS

| | | |
|---|---|---|
| DE | 297 09 504 U1 | 7/1997 |
| EP | 0 296 259 A1 | 12/1988 |
| EP | 0 332 018 A2 | 9/1989 |
| WO | WO 96/14567 A1 | 5/1996 |
| WO | WO 01/59438 A1 | 8/2001 |

OTHER PUBLICATIONS

Patent Abstracts of Japan; vol. 018, No. 688 (P–1849), Dec. 26, 1994 & JP 06 273626 A (Matsuda Denshi Kogyo:KK), Sep. 30, 1994, abstract.

* cited by examiner

*Primary Examiner*—David Porta
*Assistant Examiner*—Christine Sung
(74) *Attorney, Agent, or Firm*—Steven & Showalter LLP (57) ABSTRACT

A single vane shutter flag is asynchronously controlled so that a measuring system light source is interrupted for a minimum necessary amount of time for standardization/calibration and normalization of InGaAs system detectors. Source/detector hemispheres or serially connected randomly oriented fiber bundles homogenize light passing to the detectors. Light source testing is performed by measuring spectral power distributions at a plurality of light source power levels and comparing the measurements to baseline characteristics established for the light source. Calibration sample life is extended indefinitely by controlling the shutter flag to block source light except for short calibration time periods during which standard light levels are provided.

10 Claims, 8 Drawing Sheets

INFRARED MEASURING APPARATUS AND METHOD FOR ON-LINE APPLICATION IN MANUFACTURING PROCESSES

The invention of the present application relates to an infrared measuring apparatus and method. More specifically, the invention of the present application provides an infrared measuring apparatus having multiple Indium Gallium Arsenide (InGaAs) detectors for measuring characteristics such as moisture, fiber content, temperature, etc of a web product.

BACKGROUND OF THE INVENTION

Currently, in the manufacture of flat sheet products, such as paper, plastic films and textiles, measuring devices in production processes enable the feedback of information used in process control systems, based on measured parameters. Manual or automated process control systems may use this information. Sensors used in such process control systems may need to develop accurate measurement information on a quickly moving, fluttering web, while operating in a high humidity, dirty, hot and/or wet environment. Such sensors usually mount on measurement platforms that scan the sensors slowly in a cross-process direction as the process web moves relatively rapidly in a process direction.

Infrared spectroscopic sensors are common measuring devices for such control systems. These sensors measure the absorption of infrared radiation at specific wavelength bands, indicating a specific property's presence and/or magnitude. Specific characteristics that the sensors may measure include properties such as water, polymers, cellulose and other components of a product. A common application is the measurement of the fraction of water by weight (percent moisture) in a moving paper web during manufacturing.

The infrared spectroscopic sensor measurements utilize the differential absorption of various wavelength bands in the near infrared region, generally 0.75 $\mu$m–10.0 $\mu$m, by water and other components of the product. Process controllers compare measurements of the transmission and/or reflection of infrared energy at one or more reference wavelengths to measurements of the transmission and/or reflection at one or more absorption wavelengths. The reference wavelengths are selected for a relatively low absorption coefficient by as many of the components of the product as possible, and the absorption wavelengths are selected for a relatively high absorption coefficient. A number of different wavelength measurements may be used to determine and/or reject other interfering parameters, such as the mean optical path length through the product as a result of optical scattering. The sensors generally require the measurement of infrared energy in several spectral bands, all made simultaneously and representing the same area on the moving process. Simultaneous measurement generally requires multiple detectors, each detecting infrared energy at one of the spectral bands of interest. Since the properties of the web that affect the various infrared wavelengths can vary over short distances on the web, any differences in the web areas presented to the various detectors will result in a measurement error. Simply placing the individual detectors proximate to each other is generally inadequate to meet accuracy requirements. The signals from these detectors may be mathematically combined to develop the measurement of interest.

Conventionally, measuring systems have used lead salt detectors such as lead sulfide (PbS) or lead selenide (PbSe) detectors, however measuring systems using Indium Gallium Arsenide (InGaAs) sensors may overcome some of the complexities encountered in using lead salt detectors. InGaAs detectors are commonly used in fiber optic communications realm, and it is known to use infrared light-emitting diodes with an InGaAs device for measuring moisture value of a product. See U.S. Pat. No. 5,870,926. In contrast to lead salt detectors, InGaAs sensors are photovoltaic, so the absorption of light results in a change in voltage rather than a change of resistance as in lead salt detectors. Although both lead salt and InGaAs detectors provide good performance near room temperature, around 27 degrees C., temperature sensitivity of lead salt sensors may require maintenance of a stable sensor temperature within 0.001 degrees C. tolerance to achieve desired measurement accuracy. Since lead salt sensors are so sensitive to temperature, systems using multiple lead salt detectors must perform frequent "standardization" to correct errors produced by temperature drift and sensor dark current. Therefore, some lead salt sensors use only a single detector so the effect of temperature drift or dark current is common to all of the measured wavelengths and can be cancelled out during signal processing. This use of a single detector requires that various wavelengths are measured separately in time, possibly introducing error. InGaAs sensors have an extremely low sensitivity to temperature, less than 1/3000 that of lead salt detectors. Another known difficulty of lead salt sensors is the relatively long time constants, in the millisecond range, which limit the rate of measurement.

Existing sensors that utilize multiple detectors may use an optical beam splitter in attempts to present the same web area to all detectors. A common type of beam splitter is a partially or selectively reflecting mirror. The partial reflector transmits some fraction of the incident energy and reflects most of the remainder. If aligned properly, detectors exposed to the reflected fraction and to the transmitted fraction will "see" the same area of the web. A disadvantage of partial reflecting beam splitters is that the reduction of signal amplitude at each beam splitter limits the practical number of detectors. The selective reflecting beam splitter transmits certain wavelengths and reflects others, rather than dividing the input beam as a fraction of its amplitude, they do so according to its spectral distribution. Practical wavelength-selective beamsplitters may approach 80% efficiency, whereas partial reflective beamsplitters rarely exceed 45% efficiency. Wavelength-selective beamsplitters are more expensive than are partial reflectors and are quite sensitive to the incident angle of the optical energy, working only over a small range of angles about their design incident angle. Reflecting beam splitters also require precise positioning of all detectors.

Accordingly, there is a need for an infrared spectroscopic measuring device that overcomes or lessens these problems.

SUMMARY OF THE INVENTION

This need is met by the invention of the present application wherein an infrared spectroscopic measuring device is provided.

In one aspect of the present invention, a shutter mechanism for interrupting a light source in an infrared spectroscopic measuring device that uses light from the light source for measuring characteristics of a web of material as the web is being manufactured including a motor having an output shaft, a shutter flag coupled to the output shaft of the motor, wherein the shutter flag rotates into a position fully blocking the light source by operation of the motor and a controller for asynchronously controlling the motor to interrupt the light source is provided.

In another aspect of the present invention, a method for interrupting a light source in an infrared spectroscopic measuring device that includes at least one sensor for sensing light from the light source for measuring characteristics of a web of material as the web is being manufactured, including providing a motor having an output shaft, coupling a shutter flag to the output shaft of the motor, operating the motor to rotate the shutter flag into a position fully blocking the light source and asynchronously controlling the motor to interrupt the light source is provided.

In another aspect of the present invention, an apparatus for mixing and distributing light from a single sample portion of a web of material as the web of material is being manufactured for the simultaneous detection of a plurality of characteristics of the web including a light detector homogenizer receiving light from the sample portion and distributing that light uniformly over an output of the detector homogenizer and a light distributor receiving light from the output of the detector homogenizer and distributing portions of the light to a plurality of distributed outputs is provided.

In another aspect of the present invention, a method of testing an infrared light source for use in spectroscopic sensing systems is provided.

In still another aspect, a method of measuring at least one property of a product sample for calibration of a measuring system including illuminating the sample with a light source operating at a normal product measuring intensity, blocking the light source for a predetermined percentage of a testing period, and measuring light from the sample when the light source is not blocked is provided.

BRIEF DESCRIPTION OF THE DRAWINGS

The benefits and advantages of the present invention will become apparent to those skilled in the art to which this invention relates from the subsequent description of the illustrated embodiments and the appended claims, taken in conjunction with the accompanying drawings, in which:

DETAILED DESCRIPTION OF THE INVENTION

Figure 1A:
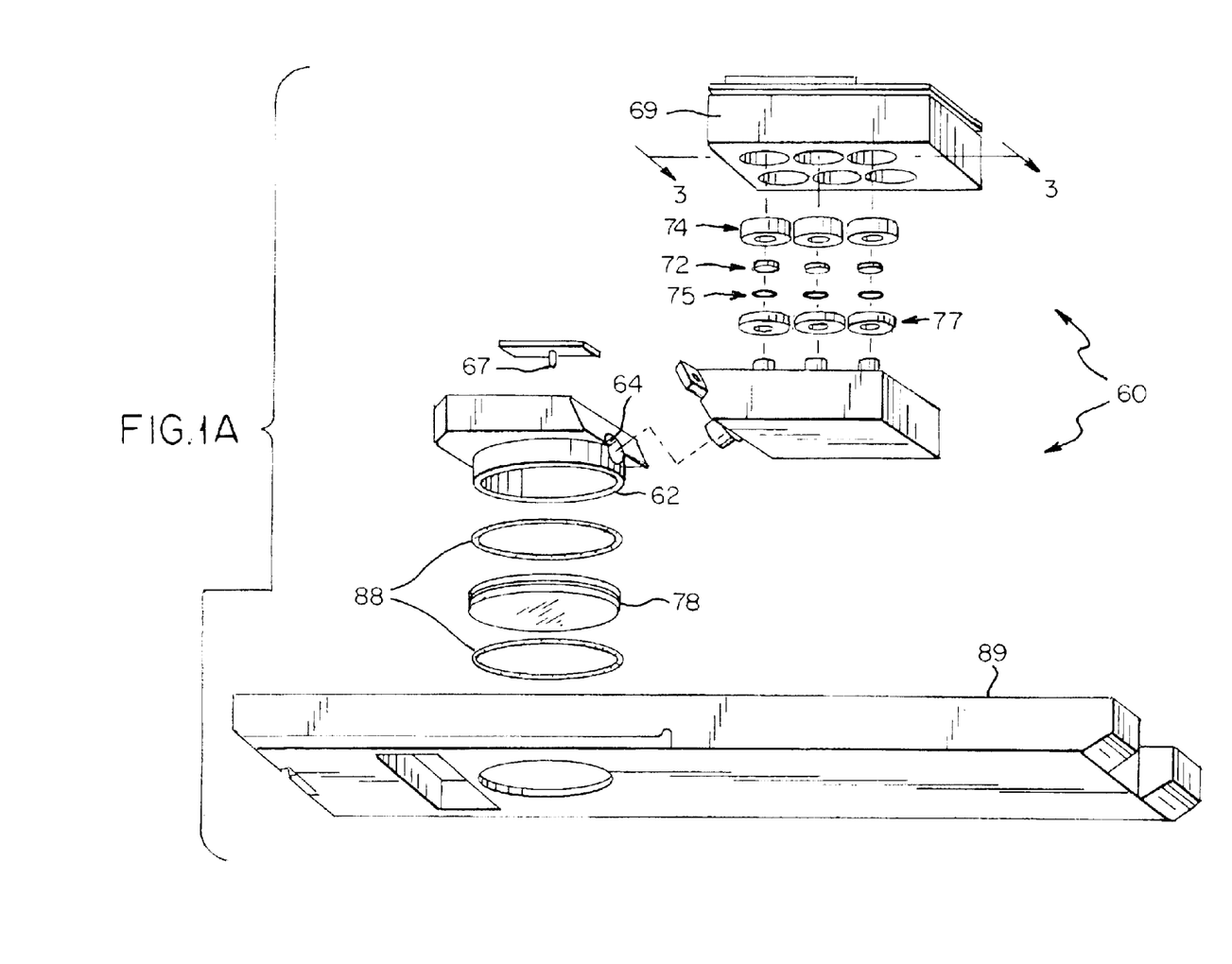
FIG. 1A is an exploded view of an illustrative embodiment of a detector assembly of an infrared measuring apparatus in accordance with the invention of the present application.
Figure 1B:
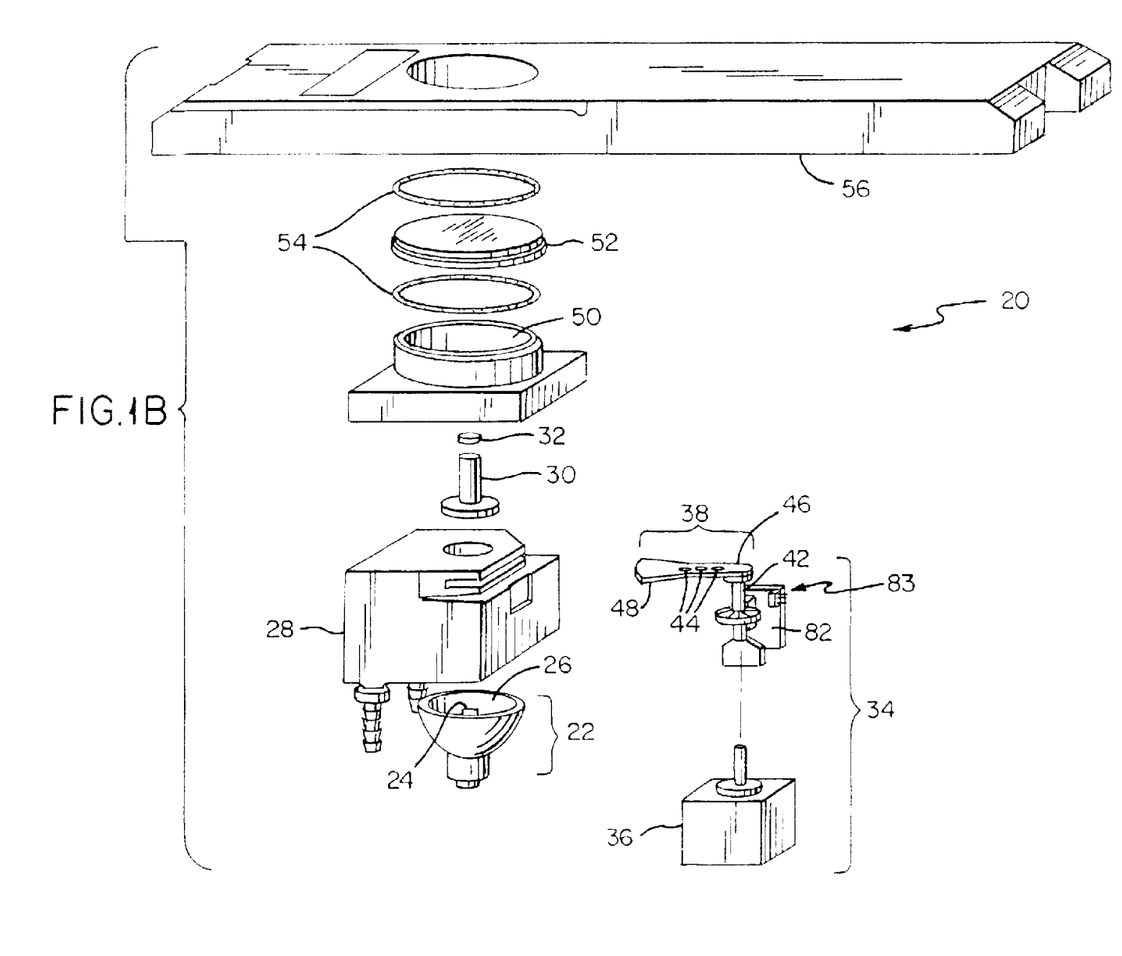
FIG. 1B is an exploded view of an illustrative embodiment of a source assembly of an infrared measuring apparatus in accordance with the invention of the present application.
Figure 2:
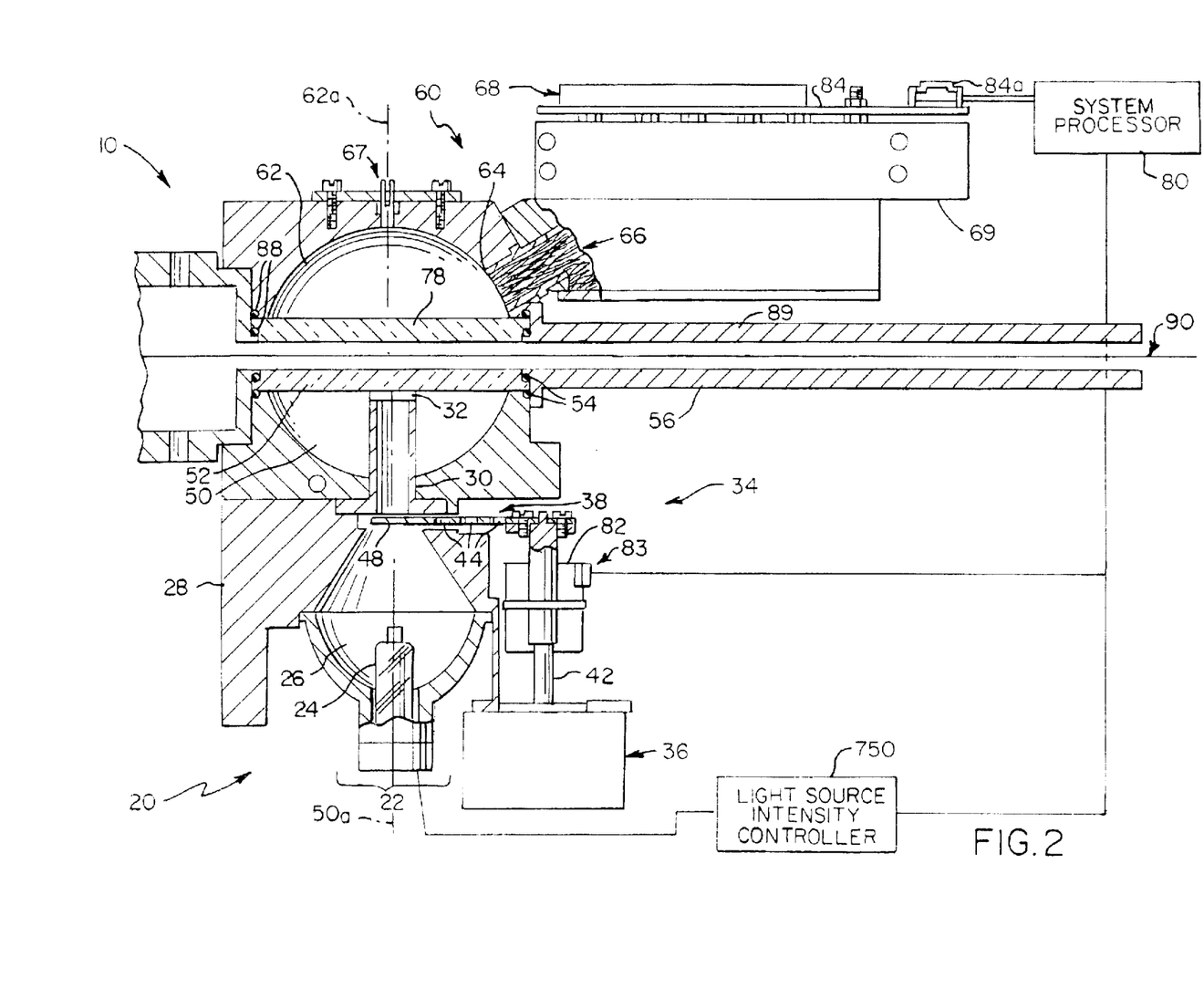
FIG. 2 is a sectioned side view of the infrared measuring apparatus of FIGS. 1A and 1B.

Referring now to the drawings, in which like-referenced characters indicate corresponding elements throughout the several views, attention is first drawn to FIGS. 1A, 1B, and 2 which show an embodiment of an infrared measuring apparatus 10 in accordance with the present invention for measuring characteristics of a web product. While the present invention is generally applicable to measurement of a variety of web products being manufactured, the present invention will be described herein with reference to a paper web 90. Infrared measuring apparatus 10 includes a source assembly 20 and a detector assembly 60.

The source assembly 20 utilizes a broad bandwidth or white light source signal (hereinafter referred to as the light source) 22 that has a light intensity that is controlled by the level of the voltage applied to the light source. The light source 22 comprises a focused projection lamp such as a tungsten halogen gold plated reflector lamp having a gold plated reflector 26 and a bulb 24 with a tungsten filament surrounded by halogen gas. Since the detector assembly 60 detects light in and near the 2 $\mu$m wavelength range, the voltage provided to the light source 22 may be reduced below a design voltage to cool the lamp and shift its emission curve away from the visible spectrum, from a design "color temperature" of about 3500K to a target of about 2600K. Thus, the light source 22 preferably emits primarily infrared light. The light source 22 preferably emits a high energy density including multiple infrared wavelengths onto a focal spot of about one centimeter diameter at a controlled focal distance from an edge of the reflector 26. The light source 22 may be air-cooled using air shroud 28 or otherwise cooled to increase lamp life and to reduce heat effects on the measuring system. The source assembly 20 also includes a light pipe 30 to direct the light from the light source 22. Additionally, a diffuser 32 may be mounted at the end of the light pipe 30 farthest from the light source 22 to reduce moisture sensitivity, if desired.

The source assembly 20 also includes a shutter mechanism 34. Shutter mechanism 34 includes a shutter motor 36, a shutter flag 38 and a shutter controller 82. The shutter flag 38 is coupled to an output shaft 42 of the shutter motor 36 so that the shutter flag 38 can be rotated into a position fully blocking the light source 22. The shutter flag 38 is shaped to minimize its angular moment of inertia while providing for proper shutter functionality. To this end, the shutter flag 38 is formed as a single vane and includes a first section 46 and a second section 48. The first section 46 of the shutter flag 38 comprises a base stalk narrower than the light source 22 and the second section 48 of the shutter flag 38 is wider than the base stalk to interrupt the light source 22. The shutter flag 38 includes at least one aperture 44 through the first section 46, three shown in the illustrated embodiment, to reduce the angular moment of the flag 38. The first section 46 of the shutter flag 38 is coupled to the output shaft 42 of the shutter motor 36. The second section 48 of the shutter flag 38 expands forming a truncated sector extending from the base stalk of first section 46 to a distal end of the shutter flag 38. The shutter flag 38 is preferably constructed of a metal, for example, titanium, aluminum or any other suitable metal. The shutter flag 38 preferably is polished on a side facing away from the light source 22 to reduce emissivity and includes a light absorbing coating on the side facing the light source 22. The light absorbing coating may be a flat black paint and may aid in conducting the resulting heat to the air and the shaft 42.

Figure 7:
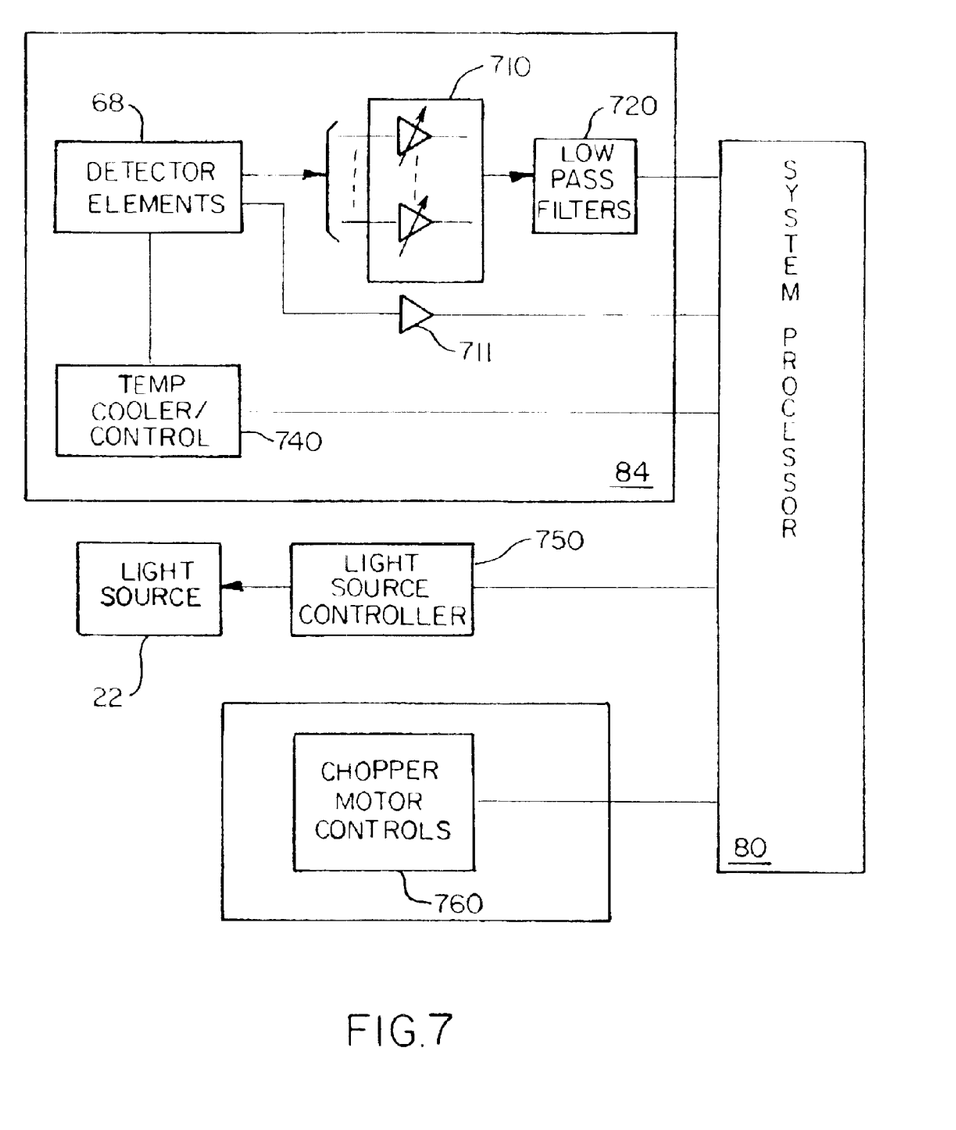
FIG. 7 is a block diagram illustrating circuitry for shutter control and detector control as well as other controller circuitry associated with the measuring apparatus of the present invention.

The shutter motor 36 is a stepper motor or other appropriate drive device that moves the shutter flag 38 so that the shutter flag 38 periodically or selectively interrupts the light source 22. The shutter controller 82 may comprise a printed circuit board and include chopper or shutter motor controls 760 having adjustable angular acceleration and maximum angular velocity parameters for asynchronously controlling the operation of the shutter motor 36. The shutter controller 82 includes a serial communication port 83 for receiving a digital control message from a system processor 80. The digital control message includes source intensity and shutter settings and performs diagnostics. The source assembly 20 may also include transducers (not shown) for monitoring temperature, "power good", and other conditions of the source assembly 20.

The source assembly 20 also includes a source light homogenizer 50 and a source window 52. The source light homogenizer 50 comprises a generally hemispherical cavity having a reflective interior surface for reflecting light towards the single sample portion of the web 90 that extends between the source assembly 20 and the detector assembly 60. The source window 52 covers the opening of the source light homogenizer 50 and may be formed of standard "Pyrex" glass having a low absorption in the wavelength used in the measuring apparatus of the present application. The source light homogenizer 50 is shaped as a truncated hemisphere to allow positioning of the source window 52 with o-rings 54 sealing the window 52 to the source light homogenizer and a base plate 56. The base plate 56 of the source assembly 20 mounts the source assembly components and provides an appropriate surface for scanning the source assembly 20 across the web 90 in the cross scan direction as the web 90 moves in the process direction.

Referring to FIGS. 1A and 2, the detector assembly 60 includes a detector light homogenizer 62 which comprises a generally hemispherical cavity having a reflective interior surface for reflecting light towards the single sample portion of the web 90 that extends between the source assembly 20 and the detector assembly 60, substantially the same as the source light homegenizer 50 in the source assembly 20. The illustrated detector assembly 60 has the capacity of housing six light detector elements 68a–68f (often identified herein generally by the reference numeral 68), see FIGS. 1A, 2, within a detector housing 69, one of which may be used for synchronization, i.e., it may serve as a "synch" detector for processing signals generated by the other detector elements, as will be described. Also see FIG. 3 which illustrates two detector elements 68a, 68c and a dummy or blank element 68e (detectors/blank elements 68b, 68d and 68f are not shown but located directly behind the two detector elements 68a, 68c and the blank element 68e shown in FIG. 3). Of course housing assemblies accommodating more than six light detector elements or fewer than six detector elements are contemplated for use in the present invention. The detector elements 68 are preferably InGaAs detectors but may be other detector technologies depending on desired properties. For example, Lead Selenide or Platinum Silicide detectors may be used if longer wavelengths are desired to be measured. It is noted that in FIG. 1A, light conveyance structures described below are shown for only the forward three light detector elements for the sake of clarity of illustration. Identical light conveyance structures are also provided for the rearward three light detector elements accommodated by the detector housing 69 of FIG. 1A.

Figure 3:
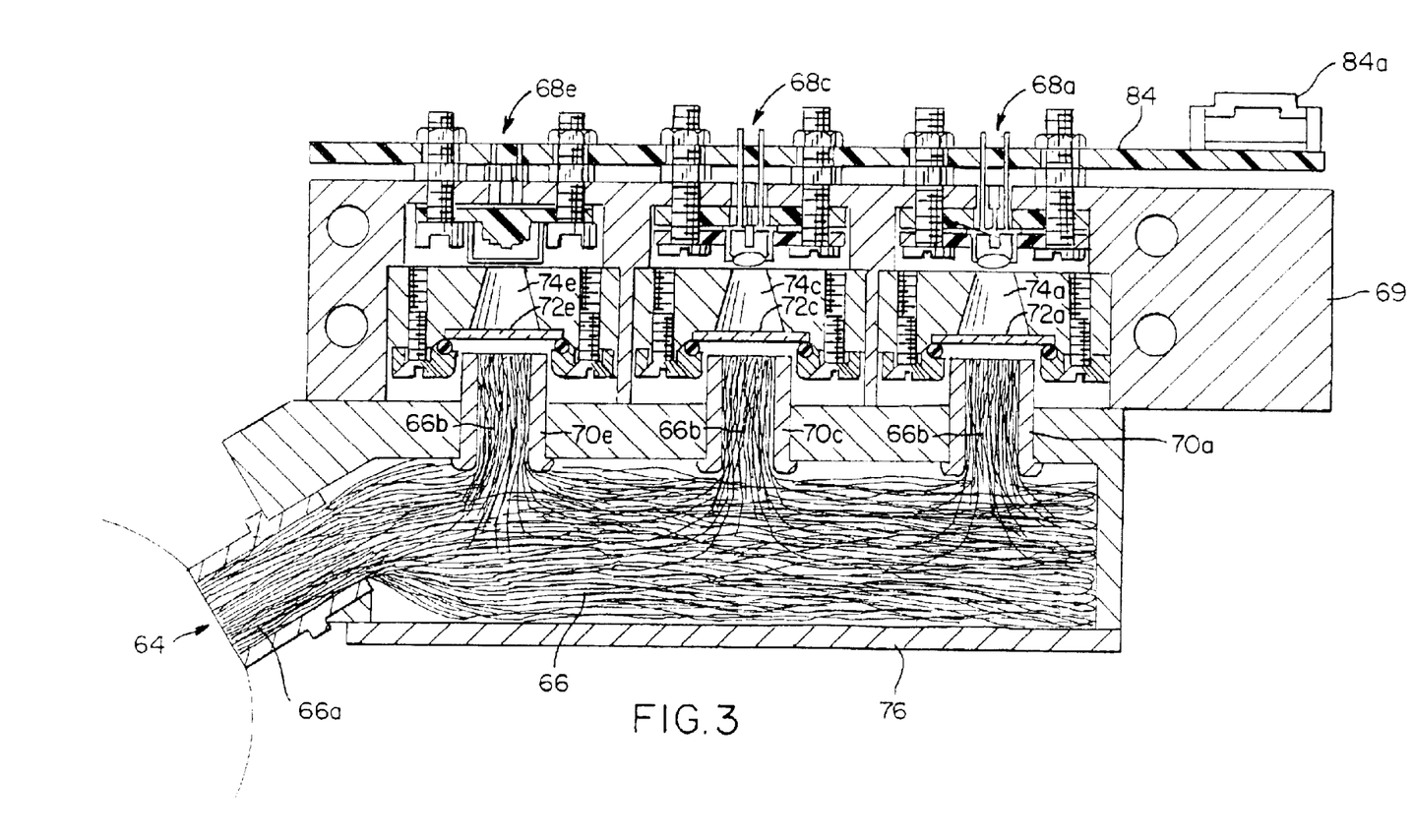
FIG. 3 is a partially sectioned side view of the detector assembly of FIG. 1A.

In a working embodiment of the present invention, four detector elements 68a–68d were used, absorption wavelength detector elements 68a, 68b and 68c (as noted above, the detector element 68b is located immediately behind detector element 68a in FIG. 3 but is not shown) and a reference wavelength detector element 68d (as noted above, the detector element 68d is located immediately behind detector element 68c in FIG. 3 but is not shown) with dummy or blank elements 68e, 68f in locations that are available to receive live detector elements (as noted above, the blank element 68f is located immediately behind blank element 68e in FIG. 3 but is not shown). One of the detector elements 68a–68f can be used for synchronization, i.e., as a "synch" detector element. However, a silicon "synch" detector 67 in a synch port of the detector light homogenizer 62, see FIGS. 1A and 2, sensitive to the visible light spectrum as well as the infrared spectrum out to 1.1 $\mu$m is used in the illustrated embodiment. The silicon "synch" detector is more sensitive than any narrow bandwidth measurement detector and is used to determine more precisely whether the shutter is opened or closed.

These detector elements 68 are discussed in greater detail throughout the description and it is understood that variations in the number and placement of the various detector elements is within the scope of the present invention. For example, an additional detector element 68 may detect temperature measurement wavelengths. The use of separate wavelength detector elements, such as the detector elements 68a–68c, enables the measuring apparatus 10 of the present invention to measure the energy at corresponding wavelengths from the same sample portion of the web substantially simultaneously allowing for simultaneous detection of a plurality of characteristics of the web 90. A detector window 78 covers the opening of the detector light homogenizer 62 and may be formed of standard "Pyrex" glass having a low absorption in the wavelength used in the measuring apparatus of the present invention. The detector light homogenizer 62 is shaped as a truncated hemisphere to allow positioning of the detector window 78 with o-rings 88 sealing the window 78 to the detector light homogenizer 62 and a base plate 89. The base plate 89 of the detector assembly 60 mounts the detector assembly components and provides an appropriate surface for scanning the source assembly 20 across the web 90 in the cross scan direction as the web 90 moves in the process direction.

Figure 2A:
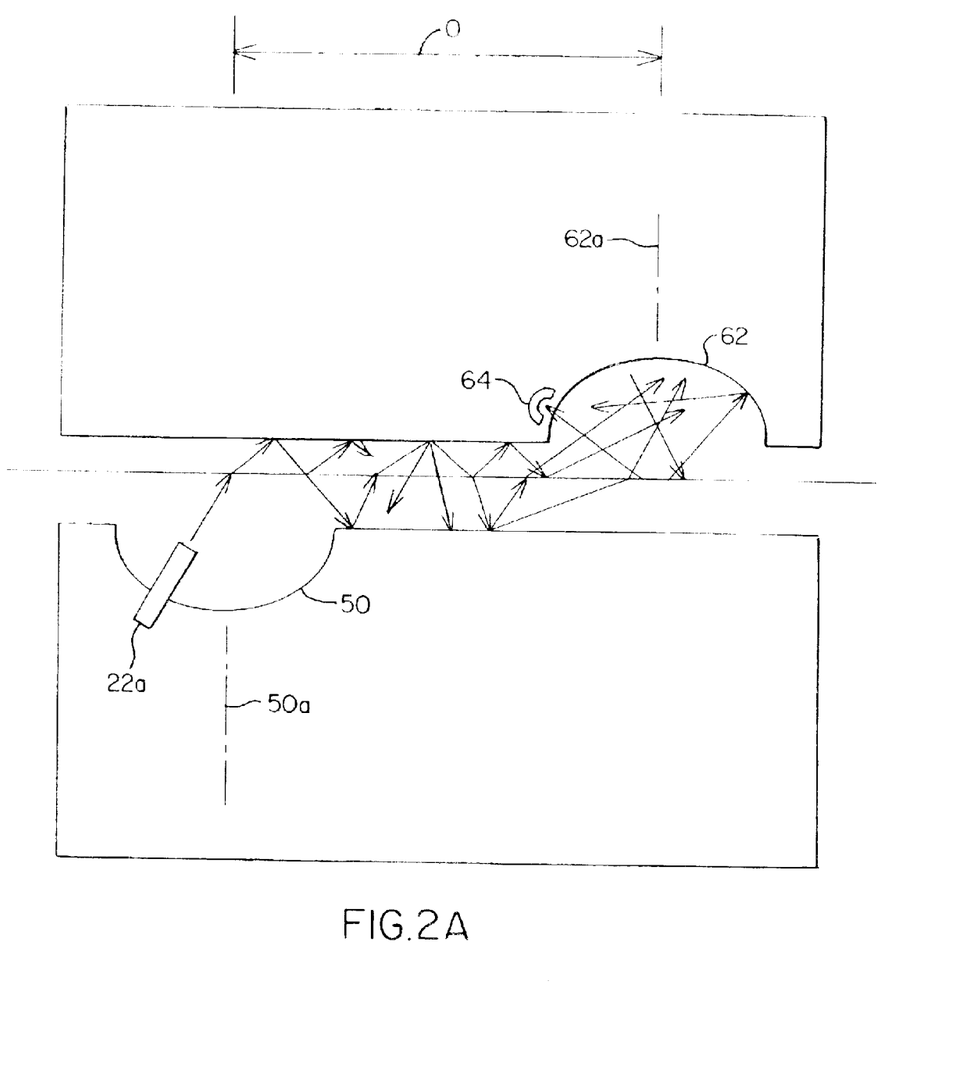
FIG. 2A is a schematic side view of an alternate embodiment of the infrared measuring apparatus of the present application showing a source light homogenizer offset from a detector light homogenizer.

In the embodiment shown in FIGS. 1A and 2, the detector light homogenizer 62 comprises a generally hemispherical cavity. The detector light homogenizer 62 includes a coating of a reflective material and acts as an optical mixing cavity for light passed through the web 90. The detector light homogenizer 62 receives light from the sample portion of the web 90 and distributes that light uniformly over an output of the detector light homogenizer 62 also known as an optical port 64. The detector light homogenizer 62 has an axis 62a substantially normal to the web 90 and the detector axis 62a may be aligned with or may be offset from the source light homogenizer 50 axis 50a normal to the web 90 by an offset o, see FIG. 2A. The schematic system of FIG. 2A illustrates an angularly oriented light source 22a and an optical port 64a located on the opposite side of the detector light homogenizer 62 to show alternate arrangements of the present invention. The detector light homogenizer 62 also includes the silicon "synch" detector 67 in the silicon "synch" port at its center.

As discussed below, the optical port 64 is oriented at an angle ranging from about zero degrees to about seventy degrees offset from the axis 62a of the detector light homogenizer 62 wherein, as described above, the axis 62a of the detector light homogenizer 62 is normal to the web 90. Preferably, the optical port 64 is oriented at an angle between about forty-five degrees and sixty-five degrees offset from the axis 62a of the detector light homogenizer 62. Additionally, a plurality of optical ports 64 may be oriented at an angle offset from an axis of the detector light homogenizer 62. For example, four optical input ports can be positioned at ninety degree intervals around the circumference of the hemisphere and located at about forty-five degree angles to the web product 90.

As shown in FIG. 3, the fraction of the homogenized light collected at the optical port 64 is input to a bundle of fiber optics 66 that are divided up to split off portions of the light input so that the portion of the light received at the optical input port 64 is distributed to a plurality of distributed outputs 70a–70f (outputs 70b, 70d and 70f not being shown). Thus, the beam splitter 76 defined by the fiber optics 66 serves as a light distributor. Specifically, the fiber optics 66 comprise a bundle 66a of randomly distributed optical fibers coupled to the optical port 64 or output of the detector light homogenizer 62 for transmitting light received at the optical port 64 to the individual detector elements 68. The bundle of randomly distributed optical fibers 66a is divided into a plurality of sub-bundles 66b with each of the sub-bundles 66b being coupled to respective ones of the distributed outputs 70a–70f. The bundle of fiber optics 66 may include hundreds of individual fibers.

Figure 4:
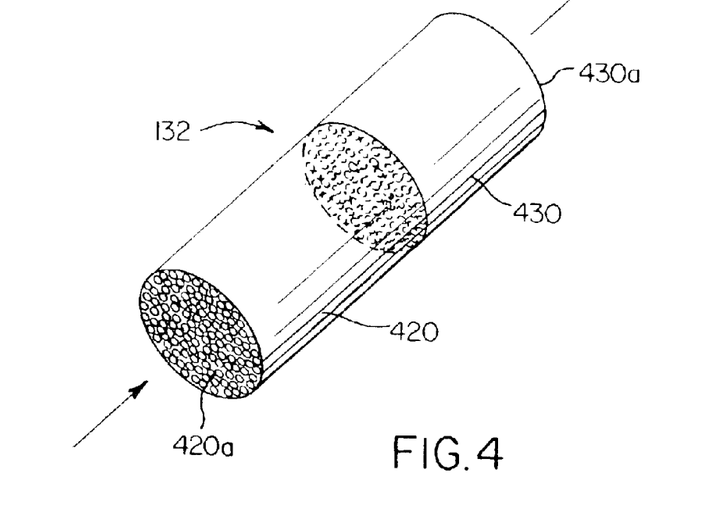
FIG. 4 is diagram of an embodiment of a detector light homogenizer including a first section of randomly distributed optical fiber bundles connected in series to a second section of randomly distributed optical fiber bundles.

FIG. 4 illustrates an alternate fiber optic light homogenizer 132 that can be used to replace or supplement one or both of the hemispherical cavities of FIGS. 1A, 1B, 2 and 2A. The fiber optic light homogenizer 132 comprises two serially connected sections or bundles of fiber optics. A first section or bundle 420 of randomly distributed optical fibers is connected in series with a second section or bundle 430 of independently randomly distributed optical fibers. Light is received at a first end 420a of the light homogenizer 132 and carried over the randomly distributed optical fibers of the bundle 420 to the randomly distributed optical fibers of the second bundle 430 which carries the light to an output 430a located at a second end of the light homogenizer 132. The first bundle 420 of randomly distributed optical fibers has an independent and hence different randomization than the second bundle 430 of randomly distributed optical fibers. The fiber lengths should be reduced to a minimum that provides an adequate randomization, and the fibers are preferably composed of special infrared transmitting fiber optic material. For any of the described embodiments, special infrared transmitting fiber optic material is manufactured by Schott Glass of Germany and may be obtained from Schott-Fostec in Auburn, N.Y.

As shown in FIG. 3, light signals from the distributed outputs 70a, 70c, 70e (only 70a, 70c, 70e of 70a–70f shown) of fiber optics 66 travel through bandpass filters 72a, 72c, 72e (only 72a, 72c, 72e of 72a–72f shown) and light collectors 74a, 74c, 74e (only 74a, 74c, 74e of 74a–74f shown), preferably conical in shape, associated with the detector elements 68a, 68c and the blank element 68e in the detector housing 69. The bandpass filters are held to the light collectors by o-rings 75 and retainers 77 secured to the light collectors. Alternatively, lenses can be used in place of the light collectors 74. The bandpass filters are tuned as closely as possible to optimize the absorption characteristics for the property each specific detector element is measuring. The beam splitter 76 is preferably adjustably mounted relative to the detector housing 69 so that the distributed outputs 70a–70f of the fiber optics 66 may be moved closer to or farther from the bandpass filters 72 to thereby control the angle of light incident on the beam splitter 76 by changing the solid angle of the fiber optics seen by the filter.

The signal detector elements 68 are mounted to a detector board 84 that includes circuitry (not shown) for processing signals generated by the detector elements 68. Note that the detector elements 68b, 68d and the blank element 68f of the illustrated embodiment are not shown in the sectioned view of FIG. 3 but for the purposes of the following discussion, are substantially identical to the corresponding elements illustrated. The signals from the wavelength detector elements 68a–68d are voltages that are functions of the measured properties or the reference value. The silicon "synch" detector 67 signal is preferably binary. The detector board 84 may be a printed circuit board and links to the system processor 80 and additional devices as necessary for system processing and adjustments. The detector board 84 includes a communication port for receiving a digital control message from the system processor 80. The digital control message includes gain, offset and calibration settings and performs diagnostics on the detectors.

Both source light homogenizer 50 and detector light homogenizer 62 assist in optimizing the basis weight and sensor alignment deflection characteristics by enabling multiple reflections through the paper web 90. Light scattering from the central infrared illuminated area of the paper web 90 that is not randomly directed toward the optical input port 64 is reflected by the source and detector light homogenizers 50, 62 towards the center, so that on a thin paper web, the average path for detected light has passed through the paper web 90 a number of times. If the paper webs to be measured are of middleweight or heavyweight, adequate optical pathlength through the web may be achieved without use of the source light homogenizer 50.

In operation, transmitted infrared light from the light source 22 projects onto a small area, hereinafter the "measured area" or single sample section, of the paper web 90 located between the source and detector light homogenizers 50, 62. The material of the paper web 90 interacts with this incident infrared light and absorbs or transmits the various spectral components in accordance with the characteristics being measured. The characteristics being measured may include any properties with specific and discrete infrared absorption bands, such as moisture, polymers, cellulose, etc. The transmitted components pass through the paper web 90 over a range of angles.

As shown in FIG. 2, the detector light homogenizer 62 is located on the side of the web 90 opposite the light source 22, and the detector light homogenizer 62 is axially aligned with the with the source light homogenizer 50 so that the geometrical center of the detector light homogenizer 62 is located at the measured area of the paper web 90. Using this configuration, light exiting the paper web 90 strikes the detector light homogenizer 62 and is reflected back towards the measured area. Some large fraction of this light may make multiple passes between the paper web 90 and the detector light homogenizer 62. Each pass of the multiple passes results in a small fraction of this light being captured by the optical input port 64 that is near the edge of the detector light homogenizer 62. These multiple reflections provide at least the following two advantages: increasing the sensitivity of the measurement by providing multiple opportunities for the light to interact with the web 90 and providing a thorough, pseudorandom mixing of the light being measured, i.e., any geometric pattern of the sampled area of the web is substantially thoroughly homogenized.

Sensitivity of this measurement of a proportionally small amount of light from the light source 22 may be increased by detecting only the light that has made many passes through or been reflected many times by the web, increasing the opportunity for absorption of the existent property. Offsetting the location of the optical input port 64 from the light source 22 increases this sensitivity. The angle of offset is measured from the axis 62a of the detector light homogenizer 62 that is normal to the web 90 and is preferably from about 45 to about 65 degrees offset, for example. However, offset angles ranging from about zero degrees to about seventy degrees can be used if desired.

The light collected at the optical input port 64 passes to the bundle of fiber optics 66 that distributes the light to the individual detector elements 68 through sub-bundles 66b which respectively illuminate each detector 68. The fiber optics 66 of the bundle 66a are randomly intermixed as suggested in FIG. 3. If there are many individual fibers and if each is small relative to the input window of each detector element 68, and finally, if the individual fibers are well mixed (preferably fiber division uniformity within better than 1%), then light output from the ends of the bundles 66a of fiber optics is uniformly divided and distributed to each detector element 68, i.e., each detector "sees" the same measured area. Such randomization also reduces the sensitivity of the infrared measuring apparatus 10 to sample flutter.

Any pattern in the geometrical distribution of the incident light at the input of the bundle 66a is further "homogenized" so that outputs of the sub-bundles 66b are uniform geometrically. It is not critical that the same number of small fiber optics be directed to each detector element 68, but the number should be large enough to provide a uniform distribution. Variation of the number of fiber optics may affect the amplitude of the light directed to each detector element 68. Thus, embodiments of the present invention use the source light homogenizer 50 and the detector light homogenizer 62 that provide optical mixing cavities and/or the fiber optic light homogenizer 132 which comprises two serially connected sections or bundles of randomized fiber optics and also the randomized fiber optic beam splitter 76 to provide homogenized light to all the detector elements 68, so that all the detector elements 68 receive light from substantially the same geometrical distribution of the measured area.

The detector elements 68 of FIG. 3 comprise multiple extended bandgap Indium Gallium Arsenide (InGaAs) detector elements 68a–68d (as noted above detector elements 68b and 68d are not visible in the sectioned view of FIG. 3 but for the purposes of the following discussion, are substantially identical to representative detector elements 68a and 68c, with exceptions noted for element 68d as discussed below). Although any size detector elements may be used in the present invention, InGaAs detector elements having a diameter of approximately one millimeter are currently preferred. The "wavelength" detector elements 68a, 68b, 68c measure infrared light over different wavelength bandpasses substantially simultaneously and output corresponding voltages. Each specific bandpass is selected to indicate the spectra absorption property of interest of a product to be measured, such as paper or plastic film. As in existing sensors, the measured frequency bands are selected from the broader band of infrared light collected by tuned dichroic interference filters, the bandpass filters 72 in the illustrated embodiment. These tuned dichotic interference filters can be tilted to shift the center wavelength of the pass bands or the angles of light passing through them can be controlled by adjusting the reflectivity of the light collectors 74 or by aperturing the fiber optics. These dichroic interference filters have different absorption coefficients for light polarized in different directions. The "synch" detector 67 in the detector assembly 60 detects the precise timing of the shutter mechanism 34 to permit accurate measurements as will be described.

As is well known in infrared spectroscopic measurement, a first wavelength or desired spectral absorption wavelength is selected where absorption is high. Then a second nearby wavelength or reference wavelength is selected where absorption is low. A function of the ratio of the infrared light at these two wavelengths transmitted through a product is proportional to the weight of the property in the measured path. For water, this measurement is converted to percent moisture by dividing the measurement by the total weight of the product in that same area. In the present invention, this total product weight is inferred from a function of the measured paper fiber weight. The actual absorption of infrared light is determined by the absorption of a standard unit of passage through the product and the pathlength of the light through the product. For example, a first InGaAs detector element is used for a fiber absorption wavelength and a second InGaAs detector element is used for a moisture absorption wavelength.

Conventional InGaAs detector elements are sensitive to infrared light no longer than about 1.7 $\mu$m in wavelength and have relatively short time constants, in the ten nanoseconds range. As mentioned above, some characteristics desired to be measured require detection of longer wavelengths. Several commercial manufacturers, such as PerkinElmer, ElectroOptics and Hamamatsu USA, offer extended InGaAs detector elements, in which the wavelength sensitivity extends to as long as 2.7 $\mu$m. A characteristic of this extension of the detected wavelength range is that certain performance parameters degrade, specifically a property commonly called the "shunt resistance". The "shunt resistance" property that permits the electrical charge produced by a detector to flow backwards through the device inserts noise into a detector's voltage signal. As the sensitive wavelength limit is extended, noise increases on the resulting detector signal. The shunt resistance varies as a function of the detector temperature, and increases rapidly as the detector temperature decreases.

Thermoelectric cooling of the active elements of each of the detector elements 68 may cause each of the detector elements 68 to operate at similar shunt resistances. Therefore, as the extension of the sensitive wavelength increases, each detector element 68 should operate at a cooler temperature. This equalizing of the operational "shunt resistance" of all detector elements 68 permits minimizing the noise floor of the overall measurement that may be made by mathematical functional combination of all detector signals, providing the optimum measurement performance.

Thermoelectric cooling devices, such as Peltier coolers, and temperature measuring devices, such as thermistors, are currently available as a built-in part of commercially available InGaAs detector elements, see temperature cooler/control in FIG. 7. Additionally, InGaAs detector elements may use compressed air heatsinking, if needed, to achieve desired cooling temperatures. Preferably, these cooling devices maintain all detector elements 68 within three degrees Celsius of their setpoint. Preferably, some of the InGaAs detector elements 68, such as elements operating at an extended wavelength, are temperature controlled while other InGaAs detector elements, such as elements operating at a non-extended wavelength, are not temperature controlled. The ability to accurately compensate for the reduced temperature sensitivity of the extended InGaAs detector elements enables multiple InGaAs detector elements 68 to obtain signals substantially simultaneously, in contrast to previous measuring devices.

In another aspect of the present invention, the operation of the shutter mechanism 34 will be discussed. The shutter flag 38 periodically blocks light source 22, allowing the residual signal at each detector element 68 to be measured in the absence of source illumination. The residual signal is the signal component not resulting from the measured parameter. Conventionally, infrared spectroscopic sensors may use signal interrupting to reduce measurement low frequency noise. Low frequency noise (ranging from DC to approximately 100 hertz) occurs due to slow drifting of detector properties and external, uncontrolled sources of incident infrared radiation. Typically in conventional infrared spectroscopic sensors, signal interrupting consists of rapid periodic interruption of the infrared source, usually by means of a spinning aperture wheel or a resonant oscillator driving a tuning fork type of shutter.

Low frequency noise, often called "1/f noise", is reduced in these conventional devices by means of tuned sequential electronics stages (filters) that eliminate the low frequency components. For example, filtering using capacitive coupling, in which a signal is passed through a serial capacitor, may effectively block the DC and low frequency components. Use of interruption signal processing is undesirable since a detector is not measuring the object to be tested while the source is blocked. In a periodically interrupting device, such as one interrupted by a tuning fork, the blocked signal may be 50% or more of the available signal. Additionally, periodic interrupting may introduce aliasing error which is a generation of false signal patterns as the interrupting frequency interferes with the sensor sampling frequency, noise or some pseudo-random pattern of the measured sampling.

The measuring apparatus 10 of the present invention uses a low, variable rate of interrupting the light source 22 with the shutter mechanism 34. The detector elements 68 take measurements when the light source 22 is fully blocked to serve as a zero determination or dark condition value. The dark condition value signals have as two major components electronic offsets inherent in each detector element 68 and any detector element 68 signal produced by ambient infrared light. Under static conditions, any ambient component may tend to remain constant and the detector related component should change very slowly as a function of temperature and long term detector drift. On a scanning system, the background may be varying and may result in a significantly varying background infrared source, thus requiring more frequent measuring of "dark condition" values. The system processor 80 then removes the dark condition value as a DC offset from the detector element 68 signal when the light source 22 is not blocked.

The shutter rate can be controlled to vary over a range of rates from 0 to about 30 chops per second with reciprocating chopping, as opposed to continuous rotary action. Preferably, the fraction of chopped time is no greater than 5% of real time. A stepper motor used as the shutter motor 36 operates asynchronously to rotate the shutter flag 38 into a position fully blocking the light source 22 and allows angular accuracy with separately controlled acceleration and maximum speed so that actual interruption dwell time can be kept constant as the chop rate varies. This relatively slow shutter rate means that no high-pass filter needs to be inserted in subsequent processing to eliminate the low frequency component. Additionally, this relatively slow shutter rate is in contrast to the 50 to 1000 interruptions per second used by conventional lead salt detectors. Nominally, the shutter flag 38 interrupts the light source 22 for durations of approximately 3–4 milliseconds at a rate of one interruption per second. The nominal shutter rate of once per second is generally adequate for maintaining electronic stability. However, this shutter rate may be inadequate for compensating for variations in background radiation. For example, a shutter rate of once per second and corresponding measuring of the dark condition value may be inadequate if there is a rapidly varying source of background infrared light (such as might be encountered in a factory situation with moving high temperature emitters in the field of view).

To provide adequate but not too frequent chopping, a default rate of one chop per second is initially used and a determination is made as to whether this chop rate is adequate or not so that the system processor 80 thus monitors and adjusts the shutter rate as needed. Generally, the required shutter rate is determined by comparing current dark conditions or corresponding baseline noise values with previous dark condition or corresponding baseline noise values. With reference to the flowchart of FIG. 5, the system processor 80 initializes index counter n and sets $\sigma_n$ to a preset baseline noise value, see step 505. Then in step 510, system processor 80 collects dark condition samples for each detector element 68 for a single shutter closure or chop. Ten to twenty of these samples should be collected for each chop depending on how much data is declared "invalid" as the shutter flag 38 moves into and out of the light source.

Figure 5:
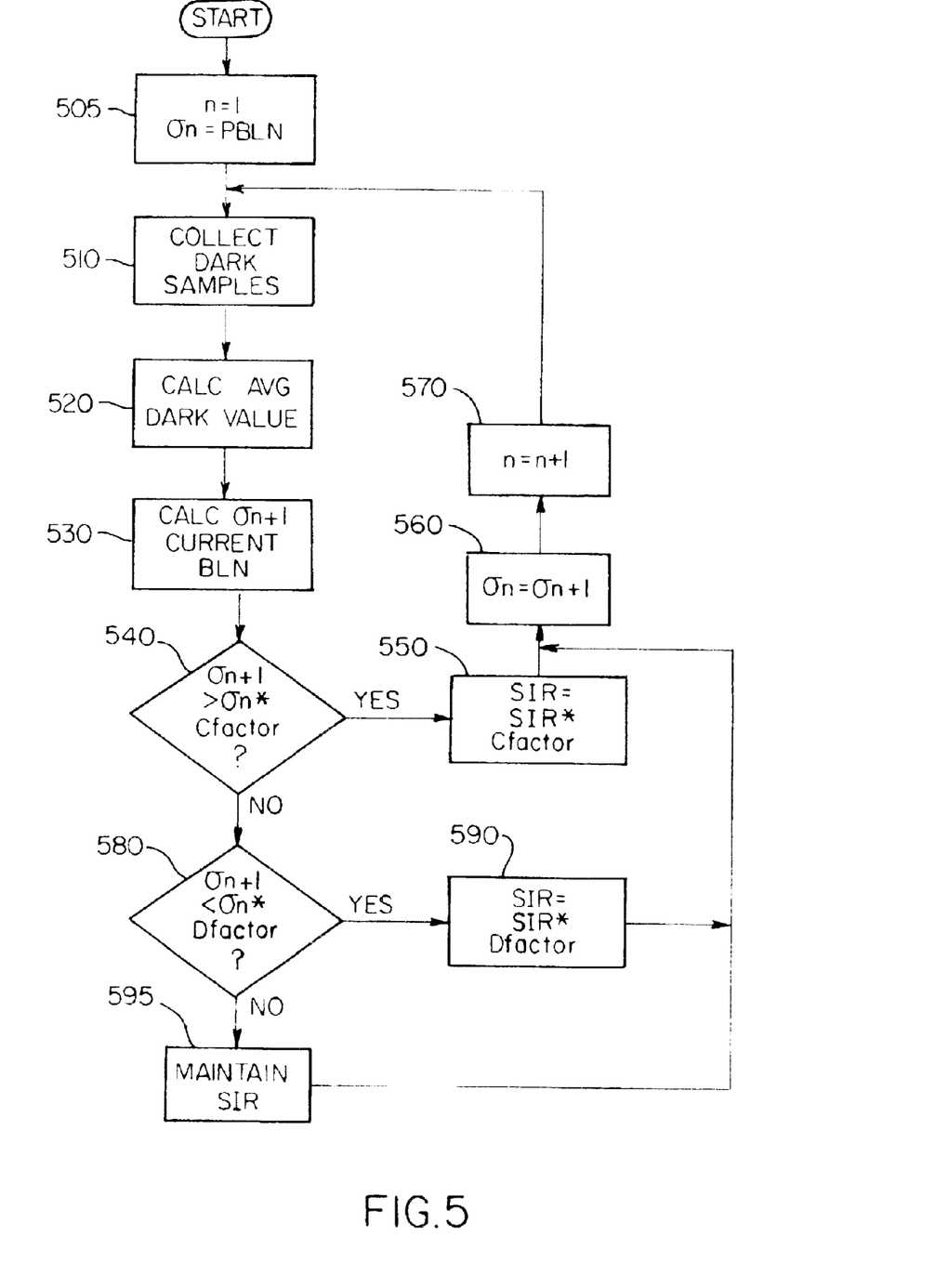
FIG. 5 is a flow chart for determining a shutter rate or shutter interruption rate for a shutter aspect of the invention of the present application.

Next, in step 520, the system processor 80 calculates an average dark condition value for these dark condition samples for each detector element 68. For example, if there are N dark condition samples collected in a single shutter:
Average Value:

$$\overline{Val} = \frac{\sum_{i=1}^{N} Samp_i}{N}$$

The system processor 80 then calculates a current noise index value or current baseline noise value, RMS variation, in step 530. For example:
Current Baseline Noise Value:

$$Noise = \sqrt{\frac{\sum_{i=1}^{N}(Samp_N - \overline{Val})^2}{N}} = \sigma_{n+1}$$

The system processor 80 then determines whether the variation in baseline noise values is greater than a first threshold value, Cfactor. This determination is made by comparing the new baseline noise value to the old baseline noise value multiplied by Cfactor as shown below and in step 540 of the flowchart of FIG. 5.

```
IF
    σ_{n+1} > Cfactor * σ_n
THEN
        New-Shutter-Rate = Old-Shutter-Rate* Cfactor
ENDIF
```

If the system processor 80 determines that the variation in baseline noise values is greater than the first threshold value, the system processor 80 signals an increase in the shutter rate by a first predetermined amount in step 550, such as by Cfactor. Thus the shutter motor 36 increases and the interruptions per unit of time of the shutter flag 38 increases. To rapidly close in on an appropriate shutter interruption rate SIR, the first threshold Cfactor can be set equal to 2, for example. The reduction in the time between baseline noise checks continues until the variation between consecutive baseline noise values is acceptable, i.e., within the limits determined by Cfactor. If the system processor 80 determines that the variation in the sequential noise index values is not above the first threshold, Cfactor, then the current shutter rate is maintained in step 595.

Alternatively, if, in step 580, the system processor 80 determines that the variation in baseline noise values is less than a second threshold value, Dfactor, the system processor 80 signals to decrease the shutter rate by a second predetermined amount in step 590, such as by Dfactor. To rapidly close in on an appropriate shutter interruption rate SIR, the second threshold Dfactor can be set equal to 0.5, for example so that the shutter rate is increased by a factor of two.

```
IF
    σ_{n+1} < Dfactor * σ_n
THEN
    New-Shutter-Rate = Old-Shutter-Rate*Dfacctor
ENDIF
```

The reduction of the shutter rate continues until the variation between baseline noise values remains acceptable and the shutter rate is reduced, perhaps to once per 5 seconds or more. If the system processor 80 calculates that the variation in the sequential baseline noise values is not below the second threshold, Dfactor, then the current shutter interruption rate is maintained in step 595. It is preferred that Cfactor and Dfactor not be substantially equivalent values to avoid oscillation or "hunting" in the control sequences.

After the system processor 80 completes each evaluation, the current baseline noise value is updated and the system index is incremented in steps 560 and 570. As shown in FIG. 5, this system of checking and adjusting the shutter interruption rate may continue as long as the measuring apparatus of the present invention operates. This system of baseline determination provides normalization functions for the detector elements 68 as the system measures each detector element's own offsets, electronic offsets and any ambient infrared light present. This system of baseline determination permits real-time correction to the signals from each detector element 68 to compensate for any measured influences.

Advantageously, there is no required periodicity or regularity to the shutter interruption rate of the shutter mechanism 34. The shutter flag 38 is individually commanded for each interrupt by a sensor control portion of the processor 80, and is controllable for rate, acceleration, and duration, i.e., the shutter flag is controlled asynchronously. The shutter flag 38 speed can be changed, even driven to zero during each check and the shutter flag 38 position can be controlled. This controllability allows the measuring apparatus 10 of the present application to maximize the fraction of time that it is measuring substantially accurately over a wide range of conditions. Preferably, the shutter control is independent of the detector sampling control with the sampling occurring substantially continuously and interrupting occurring as needed.

Using a stepper motor, as opposed to conventional AC motors, to rotate the shutter flag 38 of the present invention is a preferred way to achieve the precise control desired. The shutter motor 36 provides the ability to adjust the shutter rate from zero to approximately thirty hertz with high time resolution. The shutter motor 36 should be responsive enough to allow reciprocating blocking as opposed to continuous rotary blocking at a rate of thirty interrupts per second. This constrasts to lead salt sensors which typically use periodic blocking mechanisms such as a spinning blocking wheel or a resonant, oscillating beam to achieve the necessary high speed interrupting. Thus, the shutter flag 38 blocks the light source 22 for practically as long or as short a time as required.

Additionally, as mentioned above, the measuring apparatus 10 of the present invention preferably includes a "synch" detector in the detector module 60 to detect the precise timing of the shutter mechanism 34 so as to permit accurate measurement determination. The system processor 80 receives this silicon "synch" detector 67 signal for use in signal processing and as needed.

An actual interrupt consists of a command to start the shutter motor 36, which may be pre-configured for acceleration and speed. The shutter motor 36 accelerates the shutter flag 38 through some angle and it then enters an aperture between the light source 22 and the light pipe 30, see FIG. 2. For example, in a working embodiment, the shutter flag 38 has a total shutter passage time of 0.01 seconds with approximately 0.003 seconds of complete light source 22 occlusion or blocking. If samples from the detector elements 68 are collected at 5000 samples/second, then approximately fifteen samples may be collected when the shutter flag 38 occludes the light source 22. Since the InGaAs detector elements of the present application have a fast response time, these measurements are considered valid although it is acceptable to discard from each entering and leaving edge an additional three measurements. Thus nine dark condition samples may be used to determine measurement data. Using the above numbers, the time that the measuring apparatus 10 is not measuring characteristics of the paper web 90 is less than one percent of the operating time of the measuring apparatus 10.

Figure 6:
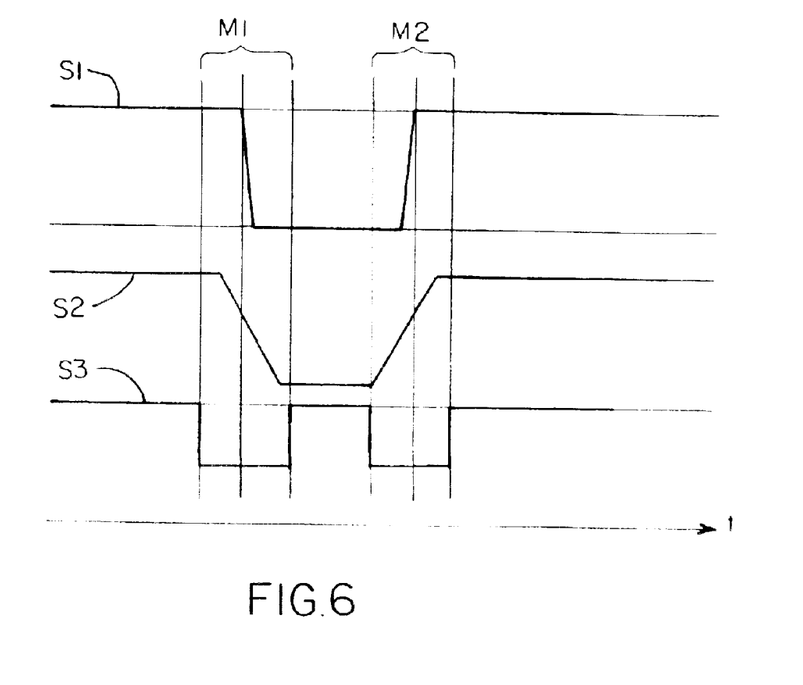
FIG. 6 is a timing diagram of a synchronization or "synch" channel relative to shutter mechanism position.

Shown in FIG. 6 are a signal S1 from the silicon "synch" detector 67, a chopper position signal S2 and a valid data signal S3. The chopper position signal is high when the shutter flag 38 is not blocking the light source 22, is low when the shutter flag 38 is blocking the light source 22 and changes from high to low and low to high as the shutter flag 38 moves toward blocking the light source 22 and changes from low to high as the shutter flag moves from blocking the light source 22. The measurements M1, M2 collected as the shutter flag 38 enters and leaves the light source 22 aperture are considered invalid and are not used in further calculations. Additional data may be discarded from each transition edge to ensure valid measurements are used.

FIG. 7 is a block diagram illustrating circuitry found on the shutter controller 82 printed circuit board, the detector board 84 as well as other controllers associated with the measuring apparatus 10. As part of the light source intensity controller, indicated as block 750 in FIG. 7, the light source 22 power supply reference voltage is preferably finely controlled at a reference level appropriate for the specific light source used and the source intensity is preferably pulse width modulated with a crystal controlled counter so that each possible level is very stable. The light source 22 power is preferably supplied as a ten kilohertz square wave AC, so that the transition time between full high and full low is negligibly short. The range of power provided for controlling the intensity of the light source 22 is preferably from zero volts to the maximum voltage level for the specific light source used, and is controlled by the light source intensity controller 750 using a latched digital command, where 0—0=0% and 1—1=100%.

Light source 22 lamp life decreases precipitously if the lamp operates at high power, i.e., near its 100% power rating. Preferably, the light source 22 operates, nominally, at 75% of its power rating, as controlled by the digital control signal from the light source intensity controller 750 discussed above. The light source 22 intensity should not be changed frequently, since each change requires a settling time for residual radiation, such as from the hot reflector, to stabilize. However, for heavy web products that highly attenuate the transmitted infrared radiation, the light source 22 intensity may be increased to reduce the required gain and resultant noise on the measurement. The light source 22 intensity is preferably determined by web grade code that is selected based on an examination of a static sample in the sensing apparatus of the present application. The web thickness corresponds to the grade code (a file containing all grade related parameters, such as target weight, target moisture, target coat thickness, etc.) of the web product and tunes the infrared measuring apparatus 10 to optimize performance on that particular product. If the noise level for measurements of a sample exceeds some predetermined level when the gain is adjusted for the proper amplitude signal, the intensity of the light source 22 should be increased. Since this is a grade code, changes should only be made during grade changes, not during normal in-grade operation.

The signals from the "wavelength" detector elements 68 preferably travel through independently controlled variable gain channel amplifiers 710, up to six of which can be provided in the illustrated embodiment (710a–710f), before being sent to the system processor 80. Since each detector element 68 channel has a dark condition value or DC offset removal means, a premeasured offset for each channel is nulled in real-time. The actual gain may differ from the nominal because of component tolerances and electronic drift. Each detector element channel includes one of the digitally controlled amplifiers 710. The amplifiers 710 preferably should be tested at each gain step and the results stored in a table of gain corrections in the system processor 80, and sent to the detector board 84 through a serial port interface (SPI). Because only the relative gains between channels are needed, an absolute reference level is not required. In a working embodiment of the invention, channel gains were adjustable between zero and ninety dB in six dB steps, a factor of two for each step. Each channel had two gain control lines, one driving gain up one step, one driving gain down one step, and both forcing gain to the center point. There were two bits that controlled each channel: 00=no change, stay latched; 01=step to 6 dB lower gain; 10=step to 6 dB higher gain; and 11=step to center gain. Software in the system processor 80 keeps track of the nominal gain setting of each channel. The actual gain is determined during a setup procedure and during operating times as needed, starting from a center point, and is stored in a "lookup" gain table in system processor 80. The values in the gain table are calculated relative to the reference wavelength channel.

Gain can be determined by adjusting the source light 22 intensity. Starting with the sensor off-line, having only air in the measurement gap (no paper web present), the light source intensity controller 750 may adjust the initial light source 22 intensity between fifty and seventy percent of maximum. The system processor 80 then centers the gain range of each detector element 68 channel and then adjusts the gain of each detector 68 channel to bring the signal values into an acceptable range centered around a preferred target value. The preferred target value is preferably the reference position and will likely differ for each detector element 68 channel. Changing the gain of any channel will result in that measured signal changing, but will have no effect on the raw signal before the channel amplifiers 710.

The independent gain capability allows the following digitizer stage to operate within its optimum (most linear) range. For example, a low mass product absorbs little, if any, of the measurement wavelengths, so that the resulting signals from the separate detector elements 68 will all be similar in magnitude. Therefore for a low mass product, the electronic gain for all of the detector elements 68 are set to substantially the same value, specifically a value that places the output signal from each amplifier 710 near the center of the input range for the digitizing circuitry in the system processor 80. On a high mass product, the wavelength that is most absorbed will produce a much smaller signal from its detector element 68 channel than will wavelengths that are only slightly absorbed. In this high mass product, different gains will be selected for each detector element 68 channel to result in similar signal output levels from each of the amplifiers 710, once again near the center range of the digitizer in the system processor 80. The digitizer output, when combined with the known gain of each detector element 68 channel, retains the required precision of measurement. This method of independent detector element 68 channel gain greatly extends the "dynamic range" of the measuring apparatus 10 of the present application by avoiding the electronic saturation of any detector element 68 channel and forcing its operation near its center scale, where it is most linear.

The adjustable gain for each individual channel amplifier introduces an electronic offset that may be amplified along with the measurement signals. To reduce the errors caused by this offset, the system processor 80 performs the following electronic correction. Initially, a command is issued that sets a bit which causes all of the measurement wavelength detector element channels to disconnect from their respective detectors and shorts the disconnected inputs to ground. In this grounded condition, only electronic offsets are available to the amplifiers. A specific high gain is selected for each channel, independently. Having selected this gain level, a command activates the auto-offset-correction. This correction routine causes the channel to seek the best available offset correction within the available resolution, and to latch this correction into a digital-to-analog converter that will supply that offset until it is reset. This correction routine should be performed for each measurement wavelength channel independently. When the correction routine is completed, the channel inputs are reconnected, restoring the channel to its measurement mode. The offset supplied by the correction digital-to-analog converter is operated on by the channel gain, so as the gain varies, the offset will remain appropriate.

To further ensure that the electronic offset is properly measured/corrected, a controlled electronic reference signal can be inserted into each measurement wavelength channel. This controlled electronic reference signal should be independently determined and applied to each channel. The insertion of the known signal set results in a known output measurement for each channel and any deviations can be corrected by the system processor 80.

Each of the detector element 68 outputs is preferably measured continuously at the nominal rate of 5000 times per second for each measurement channel. Due to the InGaAs detector elements 68 relatively fast response rates, increased measurement rates in a range of 20,000 samples per second to 1,000,000 samples per second are possible, with similarly fast response electronic systems. The "wavelength" detector element 68 channels are measured using a sixteen bit analog-to-digital converter. The calculated value of each "wavelength" detector element 68 is its measured output times the gain of its associated channel amplifier 710.

The "synch" detector element, the silicon "synch" detector 67 in the illustrated embodiment, does not require an adjustable gain amplifier so an amplifier 711 is used in the illustrated embodiment. The "synch" detector element channel varies between less than two volts, indicating the source is interrupted or blocked, and greater than four volts, indicting the source is open or on, see FIG. 6.

A single measurement of each detector element 68, collected sequentially as close in time as possible, comprises a data set. Sixteen bit analog to digital converters sample each of the detector elements 68 signals at a nominal rate of 5000 samples per second per wavelength, so that any aliasing will occur only at high frequencies, greater than 2500 Hertz. If a possible aliasing signal is detected, the signal can be easily tested to determine if it is the result of aliasing by varying the shutter interruption rate and/or the raw sample rate. As mentioned above, the relatively short time constant of InGaAs detector elements enables a relatively fast sampling rate.

Since the data acquisition occurs at an expected frequency of 200,000 times per second with various detector element outputs being sampled in an order determined by a lookup table, each detector element 68 should be offset in time from neighboring detector elements 68 by no more than $\frac{1}{200,000}$ of a second or 5 microseconds. To avoid concerns related to non-simultaneous sampling, sample and hold circuitry acquires all of the detector signals simultaneously and permits the digitization to proceed serially. Thus the illustrated system, with four "wavelength" detector elements 68a–68d and one "synch" detector 67 has an acquisition period of 20 microseconds. These data sets stream at a rate of 5000 sets/second. For a normal moving web moisture measurement, it may not be necessary to maintain this level of time resolution, so a sequential series of data sets may be accumulated before transmission from the infrared measuring apparatus' 10 local processor to a master measurement processor located remotely. However, if a high resolution optical weight measurement is desired, a full speed data set may be required.

To begin taking data measurements, the system processor 80 uses several constants and codes to perform the measurements accurately. Three quadratic coefficients for both normal and heavy ranges are included. Linearity constants and standardization constants are included for each measurement wavelength channel relative to the reference wavelength channel. Additionally, an externally input product code supplies an overall offset value and a slope value that varies with the web product being measured.

The detector board 84 preferably collects data for one millisecond, timestamps that block, and then sends it on to the system processor 80. In a single one millisecond block, there should be five sets of data from the detector board 84. Each data set will include channel signals from the "wavelength" detector elements 68a–68d and the "synch" detector element 67. All detector element channels are preferably sampled simultaneously by a sample and hold circuit. The sample and hold feature effectively eliminates data acquisition timing jitter.

To ensure accurate and reliable measurements, the measuring apparatus 10 of the present application includes standardization and normalization arrangements. Standardization is generally a periodic test of sensor operational characteristics and the required adjustment to cause the device to provide a standard (predetermined and constant) measurement under standard conditions. Normalization is generally a real-time determination of sensor operational characteristics and the required adjustments to bring those characteristics into specified limits. Thus, the dark condition value determination/control described above is a normalization process.

The measuring apparatus 10 of the present application includes the following standardization arrangement. The nominal period of standardization may be two hours although the actual standardization period may vary between once per hour and once per eight hours. To standardize, the measuring apparatus 10 is moved "off sheet", i.e., scanned off of the edge of the paper web 90, so that an air gap is in the sample measurement position. Then values of the measurement wavelength detector elements are calculated relative to the reference wavelength detector element measurement as described above. During standardization, corrections for variables, such as dirty sensor windows and channel gain variations, are made.

To determine offsets and/or gain error in the analog-to-digital front-end conversion hardware, measurements are performed while the input is shorted (zero expected) and while the input is a known, fixed value (reference voltage). Statistical noise figures can be calculated for each channel. If the noise at any channel exceeds predetermined limits, an alarm message may be set in the system controller 80.

To test for stability, the light source 22 intensity is set to a specific voltage, for example 75% of maximum. Then the gain of all measured channels is set to obtain a measured signal within a target range. After collecting measurement data, ratios for the measurement wavelength channels relative to the reference wavelength channel are calculated. These calculated ratios are compared at predetermined intervals and if the change exceeds a predetermined value, then further tests may be done. Finally, to standardize, the stability measurements are repeated to determine average values which are compared to a predetermined standardized noise limit. If the average values are within the limit, the system processor 80 uses these average values until the next standardize event occurs.

The light source 22 intensity (temperature) is varied in a carefully controlled manner so that the shift in the spectral radiation curve of the light source 22 is predictable from first principals based on Planck's blackbody curve as the filament gets hotter or colder. This spectral shift, or change in the relative distribution of energy emitted in each wavelength band, produces a measurement response. Since the degree of shift is known, the measurement response enables correction of the effect of changes in the performance of the various components, such as the independent channel amplifiers, optical filters, power supplies, etc. as well as correction for the effects of soiling of the optics. Varying the light source 22 intensity to several different values, measuring the resultant change in the spectral shift, and comparing those measurements to the shift expected permits a correction for small variations of the light source 22 filament.

Additionally, these comparisons are believed to be useful in determining the effects of small filament variations caused by aging or lamp replacement and in indicating the operational condition of the light source 22 filament. The operational condition may be used to predict the remaining service life of the light source 22.

In this regard, a tungsten filament emits light by the process of "blackbody radiation", i.e., it transfers heat energy by electromagnetic radiation. The distribution of radiant power is a function of the power or temperature, so that as the temperature varies the relative amounts of different wavelengths of emitted radiation vary proportionately. For a filament of specific electrical characteristics, the temperature reached is determined by the electrical power it dissipates and the cooling afforded by radiation, conduction and convection to its surroundings. Each increment of the filament's total active length may have a slightly different temperature, for example the ends of the filament tend to be cooled somewhat by conduction where they are attached to the filament electrodes. Further, over time as the filament is used, it slowly evaporates and the evaporation tends to be uneven so that after some use, the cross-sectional area of the filament varies along its length, i.e., there are thick and thin spots in the filament.

In the lamps used in the invention of the present application, an active scavenger halogen gas surrounds the filament. The halogen gas binds to tungsten atoms at some high temperature, and releases them at a yet higher temperature. So as the filament evaporates, the tungsten ions and atoms tend to migrate to the cooler lamp envelope where they condense into a film. The halogen gas contacting the hot lamp envelope binds to and disperses this tungsten back into the atmosphere within the lamp. When the atmosphere within the lamp contacts the much hotter filament, the bound tungsten is re-deposited onto the filament. This is the well known "tungsten-halogen cycle" and it permits the lamp envelope to remain transparent while the filament life is extended.

However, the tungsten is not re-deposited uniformly, or necessarily in the same position where tungsten previously evaporated so that eventually, the filament develops tungsten "whiskers" and some very thin spots at one of which it ultimately fails. As this redistribution of the filament material occurs, the resistance of the entire filament and individual portions of the filament varies, so that its temperature varies. This change in temperature in turn results in a different spectral distribution of radiated power so that, for a given applied voltage, the current and the spectral output changes with the age or usage of the lamp. The sensor or measuring device of the present application measures the relative power at a number of different wavelengths as its means of determining properties of the material being measured. The measuring device is, by design, extremely sensitive to small variations in spectral distribution since it is by determining these changes that it makes its measurements. So, when measuring across an air gap, no sample material present, any change in the spectral power distribution is the result of "drift" of the sensor components, including the lamp, electronics, optics and the detectors. All of these changes tend to occur slowly as the sensor ages and the optics become soiled.

If the spectral power distribution is measured at a given lamp drive voltage and then the voltage is immediately changed and the spectral power distribution is again measured, the short term variation of the spectral power distribution is primarily, almost exclusively, a function of the lamp filament. As the filament ages and undergoes the physical changes discussed above, the variation of the power distribution also changes. There is a significant difference between the variation produced by changing the voltage applied to a new, physically uniform filament and the variation produced by changing the voltage applied to a filament that has aged and become non-uniform. If this variation is measured when the lamp is new to establish baseline characteristics for the lamp and then compared to variations measured as the lamp ages, a predictive estimate of the degree of filament change can be made. This estimate permits the system processor 80 to warn the user of the sensor of filament degradation and imminent failure of the filament so that it can be replaced before it actually fails.

Another aspect of the present invention addresses the difficulty conventionally encountered when using infrared spectrometry to obtain a measurement of a static sample for calibration since the infrared light source 22 used to measure the desired properties may also heat the product being measured. Over a period of time, this heat causes the product to dry out or increases the temperature of the product, changing its infrared emission characteristics. On a moving product, such as when measuring the moisture of web of paper on a papermaking machine, this heating and/or drying does not significantly affect the measurement as the heating and/or drying does not accumulate.

However, static sample measurements, such as are used for standardization and/or normalization calibration tests as discussed above, do not pass quickly through the measuring apparatus. Therefore, the drying and/or heating may have a significant impact on the product and resultant measurement. Even products sealed within a non-water permeable barrier may be affected as the moisture migrates away from the area under test as the temperature increases.

To avoid such problems, the measuring apparatus 10 of the present invention includes control programming that can be used to adjust the intensity of the light source 22 as discussed previously. However, error might be introduced if the actual intensity of the light source 22 is reduced since measurement noise can result. Therefore, the measuring apparatus 10 of the present invention includes control programming to operate the shutter mechanism 34 in a manner to minimize the amount of time that the light source 22 illuminates samples during static measurement. Thus, the measuring method begins by operating a light source at a normal product measuring intensity and moving the product sample into a position for receiving light from the light source 22. This illuminates the sample with the light source 22 operating at a normal product measuring intensity. However, the light source 22 is blocked by the shutter flag 38 for a substantial percentage of the testing period. Finally, measurement of light from the sample occurs when the light source 22 is not blocked. The light source 22 is blocked by asynchronously moving the shutter flag 38 so that the shutter flag 38 is located between the light source 22 and the sample of the web 90. The substantial percentage of the testing period can be greater than about ninety percent and is preferably about ninety-nine percent.

The measuring method for calibration using a product sample may include moving the shutter flag 38 between the light blocking position and the non-light blocking position to control the illumination time of the product sample by the light source. In this way, the product sample is illuminated at the normal product measuring light intensity for a limited time necessary to measure at least one property of the product sample but without substantially impacting the at least one property of the product sample. For example, the shutter flag 38 blocks the light source 22 for greater than about ninety percent of testing time, so the measuring apparatus 10 makes only a low number, for example ten, measurements with the light source 22 illuminating the product sample. Preferably, the shutter flag 38 blocks the light source for about ninety-nine percent of the testing period. Thus, each of the measurements occurs at full light source 22 intensity while the heat input to the product 90 is reduced by approximately ninety-nine percent. Using this unique method, a standardization and/or normalization measurement proceeds for a substantially indefinite period of time while minimizing the average heat input to a sample.

Using this technique of controlling the shutter mechanism 34 to vary the intensity of the light source 22, the measuring apparatus 10 of the present invention diagnoses conditions of the light source 22, such as estimated remaining life. This diagnosis includes taking measurements at various known rates of shutter and either calculating or using a look-up table to estimate remaining light source 22 life. This information may be used in a preventive maintenance scheme, for example. Advantageously, the infrared measuring apparatus and method of the present invention is adaptable to both transmission and reflection mode measurements.

Although the above described embodiments describe the light source as substantially perpendicular to the product being measured, it is within the scope of the present invention to introduce the light source at an angle to the product being measured. Such angle may be opposite that of the detector optic input port, see FIG. 2A.

Although the above described embodiments describe the source assembly and the detector assembly in a substantially straight-on alignment, it is within the scope of the present invention to provide an offset between the assemblies, see FIG. 2A.

Although the invention has been described with particular reference to certain illustrated embodiments thereof, variations and modifications of the present invention can be effected within the spirit and scope of the following claims.

What is claimed is:

1. An apparatus for mixing and distributing light from a single sample area of a web of material for simultaneous detection of a plurality of characteristics of the web of material as the web is being manufactured, said apparatus comprising:

A detector light homogenizer receiving light from said sample area and distributing that light uniformly over an output of said detector light homogenizer; and A light distributor receiving light from said output of said detector light homogenizer and distributing uniformly divided portions of said light to a plurality of distributed outputs so that said plurality of distributed outputs effectively see portions of the same sample area.

2. An apparatus for mixing and distributing light as claimed in claim 1 wherein said detector light homogenizer comprises a generally hemispherical cavity having a reflective interior surface and wherein said output of said detector light homogenizer comprises an optical port oriented at an angle offset from an axis of said detector light homogenizer.

3. An apparatus for mixing and distributing light as claimed in claim 2 wherein said optical port is oriented at an angle between about zero degrees and 70 degrees from said axis of said hemispherical cavity.

4. An apparatus for mixing and distributing light as claimed in claim 3 wherein said optical port is oriented at an angle between about 45 degrees and 65 degrees from said axis of said hemispherical cavity.

5. An apparatus for mixing and distributing light as claimed in claim 2, further comprising a source light homogenizer comprising a generally hemispherical cavity having a reflective interior surface for reflecting light towards said single sample area of said web of material.

6. An apparatus for mixing and distributing light as claimed in claim 5 wherein an axis of said source light homogenizer is offset from said axis of said detector light homogenizer.

7. An apparatus for mixing and distributing light as claimed in claim 2 wherein said output of said detector light homogenizer includes a plurality of optical ports oriented at an angle offset from an axis of said detector light homogenizer.

8. An apparatus for mixing and distributing light as claimed in claim 1 wherein said detector light homogenizer comprises a first section of randomly distributed optical fiber bundles connected in series to a second section of randomly distributed optical fiber bundles, said series connected first and second optical fiber bundles receiving said light at a first end and distributing said light uniformly over said output located at a second end; wherein said first section of randomly distributed optical fiber bundles has a different randomization than said second section of randomly distributed optical fiber bundles.

9. An apparatus for collecting and distributing light as claimed in claim 1 wherein said light distributor comprises a bundle of randomly distributed optical fibers coupled to said output of said detector light homogenizer, said bundle of optical fibers being divided into a plurality of sub-bundles with each of said sub-bundles being coupled to respective ones of said distributed outputs.

10. An apparatus for collecting and distributing light as claimed in claim 9 wherein said bundle of randomly distributed optical fibers offers high transmissivity of infrared wavelengths being detected.

* * * * *